US 6,680,400 B2

(12) United States Patent
Alewelt et al.

(10) Patent No.: US 6,680,400 B2
(45) Date of Patent: \*Jan. 20, 2004

(54) CONTINUOUS PROCESS FOR THE PRODUCTION OF CARBOXYLIC ACID DIARYL ESTERS

(75) Inventors: Wolfgang Alewelt, Krefeld (DE); Steffen Kühling, Meerbusch (DE); Johan Vanden Eynde, Zwijnaarde (BE); Dirk Van Meirvenne, Chonburi (TH)

(73) Assignee: Bayer Aktiengesellschaft, Leverkusen (DE)

( \* ) Notice: Subject to any disclaimer, the term of this patent is extended or adjusted under 35 U.S.C. 154(b) by 103 days.

This patent is subject to a terminal disclaimer.

(21) Appl. No.: 10/015,432

(22) Filed: Dec. 12, 2001

(65) Prior Publication Data

US 2002/0087021 A1 Jul. 4, 2002

(30) Foreign Application Priority Data

Dec. 19, 2000 (DE) .......................... 100 63 297

(51) Int. Cl.[7] .............................................. C07C 69/96
(52) U.S. Cl. ...................................................... 558/274
(58) Field of Search ........................................ 558/274

(56) References Cited

U.S. PATENT DOCUMENTS 4,016,190 A     4/1977  Böckmann et al. ......... 260/463
6,548,691 B2 \*  4/2003  Alewelt et al.

OTHER PUBLICATIONS

Chemistry and Physics, Polymer Reviews, , H. Schnell, vol. 9, John Wiley & Sons (month unavailable) 1964, pp. 44–57 (See pp. 50/51) Chemistry and Physics of Polycarbonates.

\* cited by examiner

*Primary Examiner*—Johann Richter
*Assistant Examiner*—Paul A. Zucker
(74) *Attorney, Agent, or Firm*—Joseph C. Gil; Aron Preis

(57) ABSTRACT

An improvement to the interfacial boundary process for continuous production of carbonic acid diaryl esters is disclosed. The process that entails a reaction of monophenols in an inert solvent, in the presence of an alkaline solution and a nitrogen base catalyst, is carried out in two stages. In the first stage phosgene, inert solvent and phenol in solution are combined to form a material system and a second stage the reaction to form carbonic acid diaryl ester is completed. The improvement comprising maintaining in the first stage a pH of 11.0 to 12.0 and a temperature below 40° C. and a pH of 7.5–10.5 and a temperature <50° C. in the second stage.

5 Claims, No Drawings

CONTINUOUS PROCESS FOR THE PRODUCTION OF CARBOXYLIC ACID DIARYL ESTERS

FIELD OF THE INVENTION

The present invention relates to a process for the production of carboxylic acid diaryl esters in a continuous two-step process, in which the carboxylic acid diaryl esters are produced by the reaction of monophenols and phosgene in an inert solvent in the presence of alkali and at the phase boundary, at low reaction temperatures, and the pH of the reaction is maintained within a narrow window in each step.

SUMMARY OF THE INVENTION

An improvement to the interfacial boundary process for continuous production of carbonic acid diaryl esters is disclosed. The process that entails a reaction of monophenols in an inert solvent, in the presence of an alkaline solution and a nitrogen base catalyst, is carried out in two stages. In the first stage phosgene, inert solvent and phenol in solution are combined to form a material system and a second stage the reaction to form carbonic acid diaryl ester is completed. The improvement comprising maintaining in the first stage a pH of 11.0 to 12.0 and a temperature below 40° C. and a pH of 7.5–10.5 and a temperature below <50° C. in the second stage.

BACKGROUND OF THE INVENTION

The production of carboxylic acid diaryl esters by the phase boundary process is described in principle in the literature, e.g. in Chemistry and Physics of Polycarbonates, Polymer Reviews, H. Schnell, Vol. 9, John Wiley and Sons, Inc. (1964), pages 50/51 U.S. Pat. No. 4,016,190 describes a process for producing carboxylic acid diaryl esters which is conducted at temperatures >65° C. In this process, the pH is first of all set to a low value (pH 8 to 9) and is subsequently set to a high value (10 to 11).

In this known process, however, the purity of the product which is obtained directly leaves something to be desired, which makes costly purification operations necessary. A further problem is the high residual phenol levels in the waste water from this process, which pollutes the environment and which constitutes an increased effluent treatment problem for sewage treatment plants. Moreover, an improvement in the yield of products such as diaryl carbonates, which are produced industrially on a large scale, is always desirable.

Starting from the prior art described above, the object was therefore to provide a process which results in products of high purity in good yield, in order to reduce the purification cost thereof. The object was also to reduce the content of organics in the waste water, in order to reduce environmental pollution and to reduce the problems of treating the effluent in sewage treatment plants.

DETAILED DESCRIPTION OF THE INVENTION

It has now surprisingly been found that during the continuous production of carboxylic acid diaryl esters by the reaction of monophenols and phosgene in an inert solvent in the presence of alkali and at the phase boundary, at low reaction temperatures and at a pH of the reaction of 11–12 in the first step and at a pH of 7.5–10.5 in the second step, a high phosgene yield, a high conversion and a high degree of product purity are obtained, whilst low residual phenol levels in the waste water are achieved at the same time. Therefore, in contrast to the prior art, products of high purity can be obtained directly from the reaction. The subsequent purification process is thereby considerably simplified.

Furthermore, the low residual phenol levels make a contribution to the reduction of environmental pollution and of effluent treatment problems in sewage treatment plants.

The alkali which is used may be an aqueous alkali solution (Na, K, Li or Ca hydroxide). Aqueous sodium hydroxide is preferred, and is preferably used in the process according to the invention as a 20–55% by weight solution, most preferably as 30–50% by weight solution.

Phosgene may be used as a liquid, in gaseous form or dissolved in the inert solvent.

Suitable monophenols for use in the reaction are phenols of formula (I)

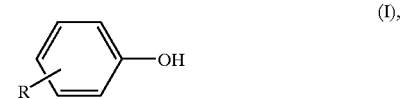

wherein
R is hydrogen, tert.-butyl, a halogen, or a branched or unbranched $C_8$ and/or $C_9$ alkyl radical.

Examples of compounds of formula (I) thus include phenol itself, alkylphenols such as cresols, p-tert.-butylphenol, p-cumylphenol, p-n-octylphenol, p-iso-octylphenol, p-nonylphenol and p-isononylphenol, and halogenated phenols such as p-chlorophenol, 2,4-dichlorophenol, p-bromophenol and 2,4,6-tribromophenol. Phenol is preferred.

Examples of inert organic solvents used in the process include dichloromethane, toluene, various dichloroethane and chloropropane compounds, chlorobenzene and chlorotoluene. Dichloromethane is preferably used.

The reaction is conducted continuously, preferably in plug flow without appreciable back-mixing. This can be carried out in tubular reactors, for example. The two phases (the aqueous and the organic phase) may be thoroughly mixed by built-in tube baffles, static mixers and/or pumps, for example.

In the first step of the continuous process according to the invention, the reaction between the reaction components is initiated by bringing together the starting materials comprising phosgene, the inert solvent, which is preferably first employed as a solvent for the phosgene, and the phenol, which has preferably already been dissolved beforehand in the aqueous alkali. The residence time in the continuous process according to the invention in the first step falls within the range from 2 seconds to 300 seconds, preferably within the range from 4 seconds to 200 seconds. The pH in the first step is adjusted by the ratio of aqueous alkali/phenol/phosgene so that the pH falls within the range from 11.0 to 12.0, preferably 11.2 to 11.8, most preferably 11.4 to 11.6. The reaction temperature in the first step is maintained at <40° C., preferably <35° C., by cooling.

In the second step of the continuous process according to the invention, the reaction to form carboxylic acid diaryl ester is completed. The residence times in the second step of the process according to the invention range between 1 minute and 2 hours, preferably between 2 minutes and 1 hour, most preferably between 3 minutes and 30 minutes. The second step of the process according to the invention is controlled by permanently monitoring the pH (in the continuous process the pH is preferably measured on-line by known methods) and by corresponding adjustment of the pH by the addition of the aqueous alkali. The amount of alkaline liquor fed in is adjusted so that the pH in the second process step falls within the range from 7.5 to 10.5, preferably 8 to 9.5, most preferably 8.2 to 9.3 The reaction temperature in the second step is maintained at <50° C., preferably <40° C., most preferably <35° C., by cooling.

The general or preferred parameters or data which is given in the present Application can also be arbitrarily combined with each other, however, namely combinations of general and preferred parameters can be made.

The aqueous phase of the process according to the invention then contains less than 250 ppm, preferably less than 150 ppm, more preferably less than 100 ppm phenol, most preferably less than 50 ppm phenol.

In the process according to the invention, phosgene is employed in a ratio of 1.01 to 1.15 mol %, preferably 1.05 to 1.12 mol %, with respect to the phenol. The solvent is admixed so that after reaction the carboxylic acid diphenyl ester exists as a 5 to 60% solution, preferably as a 20 to 45% solution, the percents being relative to the weight of the solution.

The reaction may be speeded up by catalysts, such as tertiary amines, N-alkylpiperidine or onium salts. Tributylamine, triethylamine and N-ethylpiperidine are preferably used. The concentrations of the catalysts are from 0.0001 mol to 0.1 mol with respect to the phenol used.

In the present Application, onium salts are understood to be compounds such as $NR_4X$, wherein R can be an alkyl and/or aryl radical and/or an H atom and X is an anion.

After the reaction, the organic phase which contains the carboxylic acid diaryl ester is usually washed with an aqueous liquid and is separated from the aqueous phase as far as possible after every washing operation. Washing is preferably effected using deionised water. After washing and separation of the washing liquid, the solution of carboxylic acid diaryl ester is usually turbid. Aqueous liquids are used as washing liquids for the separation of the catalyst, e.g. a dilute mineral acid such as HCl or $H_3PO_4$, and deionised water is used as a washing liquid for further purification. The concentration of HCl or $H_3PO_4$ in the washing liquid can amount to 0.5 to 1.0% by weight, for example. The organic phase is preferably washed twice, for example.

Separating vessels, phases separators, centrifuges or coalescers which are known in principle, or even combinations of these apparatuses, can be used as phase separation apparatuses for the separation of the washing liquid from the organic phase.

Without taking into consideration the solvent which is still to be separated, surprisingly high degrees of purity of the carboxylic acid diaryl ester of >99.85% (measured by GC) are obtained in this manner.

In order to obtain the high purity carboxylic acid diester, the solvent is evaporated. Evaporation can be effected in a plurality of evaporation steps, e.g. by employing one or more distillation columns in series in which the solvent is separated from the carboxylic acid diaryl ester.

These purification step or steps can be conducted continuously, for example, so that the bottom temperature during distillation ranges from >150° C. to 310° C., preferably from >160 to 230° C. The pressures which are necessary for carrying out said distillation range between 1 and 1000 mbar, preferably between 5 and 100 mbar.

The carboxylic acid diesters are distinguished by their particularly high purity (>99.95% as measured by GC) and by their extremely good transesterification properties, so that an excellent quality of polycarbonate can be produced.

The use of carboxylic acid diaryl esters for the production of aromatic oligo-/polycarbonates by the melt transesterification process is known from the literature, and has been described previously, for example, in the Encyclopedia of Polymer Science, Vol. 10 (1969), in Chemistry and Physics of Polycarbonates, Polymer Reviews, H. Schnell, Vol. 9, John Wiley and Sons, Inc. (1964) and in U.S. Pat. No. 5,340,905.

The following examples illustrate the present invention without limiting it.

EXAMPLES

Example 1

A mixture comprising 103 kg/hour of deionised water, 42.2 kg/hour 50% NaOH and 48.3 kg/hour phenol was continuously combined with a solution comprising 86.2 kg/hour methylene chloride and 27.5 kg/hour phosgene (8 mol % excess with respect to phenol) in a vertical, cooled tubular reactor. The reaction mixture was cooled to a temperature of 33° C., and a pH of 11.5 was measured after an average residence time of 15 seconds. 5.4 kg/hour of 50% NaOH were then added to said reaction mixture in the second step of the process, so that after a further residence time of 5 minutes the pH in the second reaction step was 8.5. In this continuously operated reaction, any fluctuations in the rates of addition which occurred were compensated for by adjusting the rate of addition of NaOH in each case. In the second step of the process, the reaction mixture was continuously mixed by passing it through a tube provided with constrictions. After the renewed addition of NaOH, the reaction temperature was adjusted to 30° C. by cooling. The aqueous, slightly alkaline phase contained 20 ppm phenol. The DPC yield was correspondingly high, namely 99.998% with respect to phenol. After separating the organic phase from the aqueous phase, the product was washed with 0.6% HCl and water, and 99.9% (as determined by GC) diphenyl carbonate was obtained after a final phase separation after removing the methylene chloride by evaporation.

Comparative Example 1

The procedure was as in Example 1, except that no cooling was employed in the second step of the process, so that the reaction temperature was 60° C. The aqueous, slightly alkaline phase then contained 2400 ppm phenol. Accordingly, the DPC yield with respect to phenol was only 99.76%.

Comparative Example 2

The procedure was as in Example 1, except that 7.8 kg/hour of 50% NaOH was metered in instead of 5.4 kg/hour, so that the pH in the second reaction step was 11.7 after a further residence time of 5 minutes. The aqueous, slightly alkaline phase then contained 900 ppm phenol. Accordingly, the DPC yield with respect to phenol was only 99.91%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. In the interfacial boundary process for continuous production of carbonic acid diaryl esters from phosgene and monophenols in an inert solvent, in the presence of an alkaline solution and a nitrogen base catalyst, the process including a first stage wherein phosgene, inert solvent and phenol in solution are combined to form a material system and a second stage wherein the reaction to form carbonic acid diaryl ester is completed, the improvement comprising maintaining in the first stage a pH of 11.0 to 12.0 and a temperature below 40° C. and a pH of 7.5–10.5 and a temperature <50° C. in the second stage.

2. The process of claim 1 wherein the pH in the first process stage is 11.2 to 11.8 and the pH in the second stage is 8 to 9.5.

3. The process of claim 1 wherein the pH in the first process stage is 11.4 to 11.6 and the pH in the second stage is 8.2 to 9.3.

4. The process of claim 1 wherein the temperature in the first process stage is maintained at <35° C. and in the second stage is maintained at <40° C.

5. The process of claim 1 wherein the temperature in the second stage is maintained at <35° C.

* * * * *